(12) United States Patent
Sweeney et al.

(10) Patent No.: US 10,595,907 B2
(45) Date of Patent: Mar. 24, 2020

(54) POLYAXIAL PEDICLE SCREW

(71) Applicant: Rubicon Spine LLC, Sarasota, FL (US)

(72) Inventors: Thomas M. Sweeney, Sarasota, FL (US); Tan Duy Ly, Sarasota, FL (US); Hon Quynh Vien, Richmond, IN (US); Michael T. Boyer, Venice, FL (US); John D. Kuczynski, Sarasota, FL (US)

(73) Assignee: Rubicon Spine LLC, Sarasota, FL (US)

( * ) Notice: Subject to any disclaimer, the term of this patent is extended or adjusted under 35 U.S.C. 154(b) by 145 days.

(21) Appl. No.: 15/686,683

(22) Filed: Aug. 25, 2017

(65) Prior Publication Data
US 2018/0228517 A1 Aug. 16, 2018

Related U.S. Application Data

(60) Provisional application No. 62/600,239, filed on Feb. 16, 2017.

(51) Int. Cl.
*A61B 17/70* (2006.01)
*A61B 17/86* (2006.01)
*A61B 17/80* (2006.01)

(52) U.S. Cl.
CPC ........ *A61B 17/7041* (2013.01); *A61B 17/705* (2013.01); *A61B 17/7032* (2013.01); *A61B 17/7035* (2013.01); *A61B 17/7059* (2013.01); *A61B 17/7076* (2013.01); *A61B 17/7091* (2013.01); *A61B 17/8033* (2013.01); *A61B 17/8605* (2013.01); *A61B 17/8685* (2013.01)

(58) Field of Classification Search
CPC ............ A61B 17/7032; A61B 17/7035; A61B 17/7041; A61B 17/705; A61B 17/7061; A61B 17/7059; A61B 17/7091; A61B 17/8033; A61B 17/8685
See application file for complete search history.

(56) References Cited

U.S. PATENT DOCUMENTS

| 8,100,947 | B2 | 1/2012 | Ensign et al. | |
|---|---|---|---|---|
| 8,100,948 | B2 | 1/2012 | Ensign et al. | |
| 9,232,965 | B2 | 1/2016 | Hawkes | |
| 2006/0147129 | A1* | 7/2006 | Miller | B65D 75/5838 383/205 |
| 2008/0015597 | A1* | 1/2008 | Whipple | A61B 17/7037 606/250 |
| 2008/0058812 | A1* | 3/2008 | Zehnder | A61B 17/7004 606/254 |
| 2008/0147129 | A1* | 6/2008 | Biedermann | A61B 17/7032 606/308 |

(Continued)

*Primary Examiner* — Matthew J Lawson
(74) *Attorney, Agent, or Firm* — Kim IP Law Group PLLC

(57) ABSTRACT

A polyaxial bone anchor is disclosed. The polyaxial bone anchor comprises a receiver member that includes an open bottom, a first locking member and a first sidewall. The open bottom receives a shank having a substantially spherical head. The first sidewalls has a first recess which is configured to receive the first locking member. The receiver member can further include a rod receiving recess, a second locking member, and a second sidewall. The rod receiving recess receives a rod. The second sidewall has a second recess for receiving the second locking member.

28 Claims, 26 Drawing Sheets

(56) References Cited

U.S. PATENT DOCUMENTS

| | | | |
|---|---|---|---|
| 2008/0243185 A1* | 10/2008 | Felix | A61B 17/7032 606/246 |
| 2008/0243193 A1* | 10/2008 | Ensign | A61B 17/7032 606/305 |
| 2009/0105770 A1* | 4/2009 | Berrevoets | A61B 17/7032 606/308 |
| 2010/0152785 A1* | 6/2010 | Forton | A61B 17/7035 606/301 |
| 2013/0172937 A1* | 7/2013 | Davenport | A61B 17/7032 606/278 |
| 2014/0214097 A1* | 7/2014 | Jackson | A61B 17/7037 606/305 |
| 2016/0038204 A1* | 2/2016 | Biedermann | A61B 17/8605 606/305 |
| 2018/0303519 A1* | 10/2018 | Liu | A61B 17/70 |

* cited by examiner

POLYAXIAL PEDICLE SCREW

CROSS REFERENCE TO RELATED APPLICATIONS

The present application claims the benefit of U.S. Provisional Patent Application No. 62/600,239, entitled "Robotics Friendly Polyaxial Pedicle Screw" filed on Feb. 16, 2017, the entire disclosure of which is incorporated herein by reference.

BACKGROUND OF THE INVENTION

The following exemplary embodiments of the present invention relate generally to polyaxial pedicle screws and, more specifically, to a polyaxial pedicle screw that includes a receiver member having a pair of recesses and a pair of locking members for independently securing a rod and a shank.

Polyaxial pedicle screws are commonly used for lumbar fusion surgery. Such screws are configured to receive additional equipment or implants, such as a stabilization rod, either before or after being anchored to the bone via, e.g., a screw or shank. The positioning and alignment of the screw dictates the location and orientation of the additional equipment. In a spinal stabilization procedure, a plurality of pedicle screws are mounted to vertebrae and one or more rods extend between the fasteners so as to immobilize a portion of the spine.

Because pedicle screws are often used for lumbar fusion surgery, precision in the implantation of the screw is of utmost importance. Therefore, robots are sometimes used to assist in the placement and securing of these screws.

Typical polyaxial pedicle screws use a locking cap that threads into a tulip body of the polyaxial pedicle screw to apply a compressive force to the rod and the shank to simultaneously lock the motion of the rod and the shank. Other, more current designs, use a "collet" or other mechanism to independently lock the polyaxial motion of the shank and the motion of the rod.

BRIEF SUMMARY OF THE INVENTION

In accordance with an exemplary embodiment, the subject disclosure provides for a polyaxial bone anchor comprising a receiver member. The receiver member includes an open bottom, a first locking member and a first sidewall. The open bottom member receives a shank having a substantially spherical head. The first sidewall has a first recess configured to receive the first locking member.

An aspect of the exemplary embodiment is that the receiver member further includes a second sidewall having a second recess configured to receive a second locking member. The receiver member further includes a rod receiving recess formed by at least one of the first and second sidewalls. The second sidewall is movable between first and second positions. The second locking member is configured to press-fittingly engage the second recess.

Another aspect of the exemplary embodiment is that the first locking member is slidable within the first recess. The polyaxial bone anchor further comprises a shank having a substantially spherical head. The first locking member is configured to engage the substantially spherical head when the first locking member is received within the first recess and the shank is received within the open bottom. The first locking member is configured to press-fittingly engage the substantially spherical head when the shank is received within the open bottom. The first locking member includes a curved surface configured to engage the substantially spherical head of the shank when the shank is received within the open bottom.

Another aspect of the exemplary embodiment is that the first recess is in fluid communication with the open bottom. The receiver member further includes a rod receiving recess. The first locking member is a locking wedge. The polyaxial bone anchor further comprises a percutaneous driver extending from the receiver member. The percutaneous driver includes an elongated body having a proximal end connected to the receiver member, and a driver slidable along the elongated body for engaging the first locking member. The percutaneous driver is connected to the receiver member about a weakened portion for separating from the receiver member. The percutaneous driver is connected to the first locking member about a weakened portion for separating from the first locking member.

In accordance with another exemplary embodiment, the subject disclosure provides a polyaxial bone anchor system comprising a shank, a rod and a receiver member. The shank has a rounded head. The receiver member includes a first press-fit locking mechanism and a second press-fit locking mechanism. The first press-fit locking mechanism engages the shank. The second press-fit locking mechanism engages the rod.

An aspect of the exemplary embodiment is that the receiver member further includes a body having a first recess and a second recess, wherein the first press-fit locking mechanism comprises the first recess and a first locking member, and wherein the second press-fit locking mechanism comprises the second recess and a second locking member. The body further includes a rod receiving recess for receiving the rod. The rod receiving recess is positioned between the first and second press-fit locking mechanisms. The shank further includes a shank body, and the rounded head is offset from a longitudinal axis of the shank body.

In accordance with another exemplary embodiment, the subject disclosure provides a rod connector comprising a first receiver member portion. The first receiver member portion includes a first rod receiving recess, a first locking member and a first sidewall. The first rod receiving recess receives a first rod. The first sidewall has a first recess for receiving the first locking member.

An aspect of the exemplary embodiment is that the first sidewall is movable between first and second positions. The rod connector further comprises a second receiver member portion adjacent the first receiver member portion. The second receiver member portion includes a second rod receiving recess, a second locking member and a second sidewall. The second rod receiving recess functions to receive a second rod. The second sidewall has a second recess for receiving the second locking member. The first rod receiving recess if formed by the first sidewall and the second rod receiving recess is formed by the second sidewall. Each of the first sidewall and the second sidewall is movable between first and second positions.

BRIEF DESCRIPTION OF THE SEVERAL VIEWS OF THE DRAWINGS

The foregoing summary, as well as the following detailed description of the exemplary embodiments, will be better understood when read in conjunction with the appended drawings. For illustration purposes, there are shown in the drawings exemplary embodiments. It should be understood, however, that the subject disclosure is not limited to the precise arrangements and instrumentalities shown.

DETAILED DESCRIPTION OF THE INVENTION

Figure 1A:
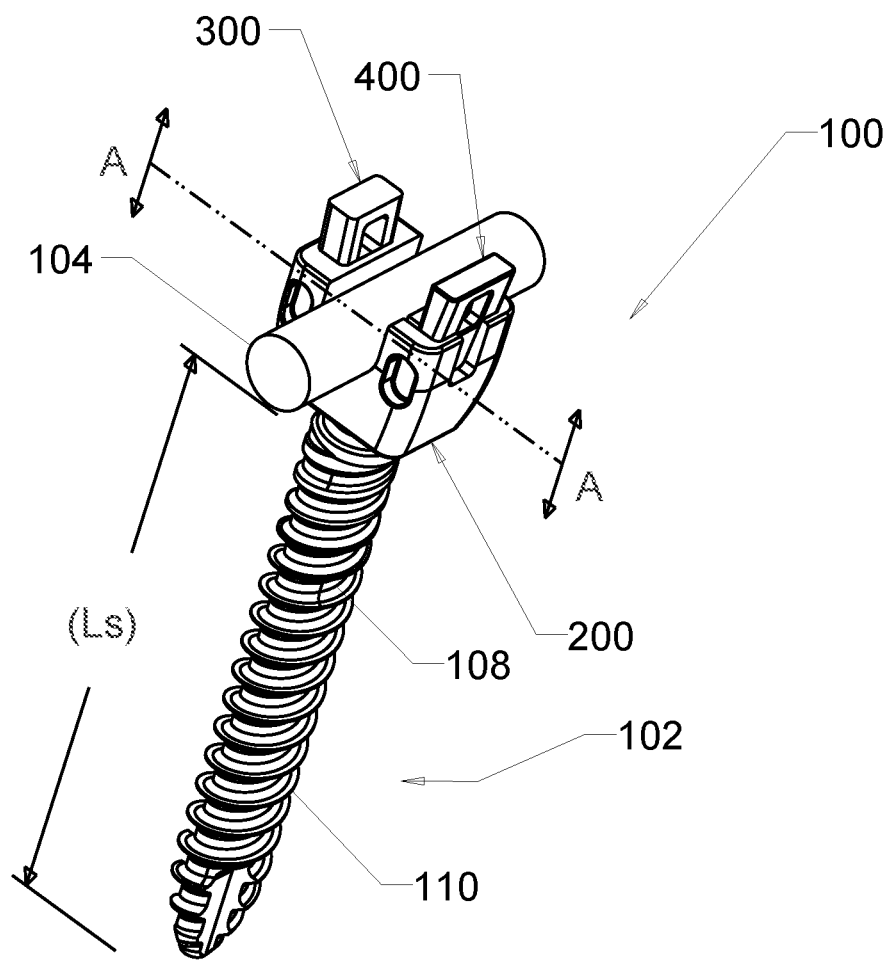
FIG. 1A is a perspective view of a polyaxial bone anchor in accordance with an exemplary embodiment of the subject disclosure.

Reference will now be made in detail to the various exemplary embodiments illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below, front, real, and diagonal, are used with respect to the accompanying drawings. The terms "right," "left," "front," and "rear" are used to describe positions relative to an operator. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various aspects of the exemplary embodiments can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments.

Additionally, for convenience purposes only, different exemplary embodiments having substantially identical elements will be differentiated with a "'," e.g., a polyaxial bone anchor 100', and may be described with reference to only one exemplary embodiment, e.g., a polyaxial bone anchor 100. It is appreciated therefore that the description of the primary exemplary embodiment and its sub elements is equally applicable to the alternate embodiments and their sub elements, except where otherwise indicated. As such, identical elements, or substantially identical elements where so indicated, will be identified, where appropriate, by the same reference number, e.g., 100, and distinguished by "'", for example, 100', 100", 100''', and so forth.

Referring now to FIGS. 1A-6B, there is illustrated a polyaxial bone anchor 100 in accordance with an exemplary embodiment of the subject disclosure. The polyaxial bone anchor comprises a receiver member 200, e.g., a tulip body, a first locking member 300, a second locking member 400, a shank 102, a rod 104 and a percutaneous driver 600.

Referring now to FIGS. 1A-2C, in accordance with an exemplary embodiment, the receiver member 200 is configured substantially as shown, having a tulip body configuration. The receiver member includes an open bottom end 202, a rod receiving recess 204, a pair of diametrically opposed first and second sidewalls 206, 208, a first recess 210 and a second recess 212.

The open bottom end 202 is configured to receive the shank 102, and more specifically a head 106 of the shank. Thus, the open bottom end 202 is defined as a through hole extending through the bottom of the receiver member 200 having an inner surface 214, an open bottom portion 216 and an open top portion 218. The open bottom end 202 defines a cavity 240 that receives the head 106 of the shank 102. A portion of the inner curved surface 214 of the cavity 240 is configured to have a concave shape complementary to the shape of the head 106 and positioned diametrically opposed to the first sidewall 206 as seen in FIG. 1D.

The open bottom end 202 is sized and shaped to receive the shank's head 106 through the open bottom portion 216. It is appreciated, however, that the open bottom end 202 and the shank head 106 can have, e.g., an oval shape so as to permit the shank head 106 to be rotatably inserted into the open bottom end 202, as described in greater detail below.

The rod receiving recess 204 is configured to receive the rod 104 and is defined by the first and second sidewalls 206, 208, and the open top portion 218 of the open bottom end 202. The rod receiving recess 204 includes an open top portion 220 and extends completely through the receiving member 200 forming diametrically opposed slots 222, 224 extending between the first and second sidewalls 206, 208. In accordance with an exemplary aspect, the rod receiving recess 204 is in fluid communication with the open bottom end 202 via, e.g., the open top portion 218.

It is appreciated that the open top portion 218 may optionally include threads, fasteners, grooves or other such elements to facilitate a more secure connection between the rod 104 and the shank 102. In an exemplary embodiment, the open top portion 218 of the open bottom end 202 has concavely curved diametrically opposed surfaces to receive both the rounded head 106 of the shank and the rod 104 at their respective sides of the open top portion 218.

The first sidewall 206 includes the first recess 210 to receive the first locking member 300. The first recess 210 extends through the first sidewall 206 and is in fluid communication with the open bottom end 202. In other words, the first recess is in fluid communication with the open bottom. In an exemplary embodiment, a portion of the first recess 210 and the open bottom end 202 collectively form a cavity sized and shaped to permit passage of the shank head 106.

The first sidewall 206 may further include a fastener 226 configured to be attachable to a tool for moving the receiver member 200. In an exemplary embodiment, the fastener 226 is a groove. The first sidewall 206 further includes an aperture 228 which is in communication with the first recess 210. In an exemplary embodiment, the aperture 228 is on an outside wall 230 of the receiver member 200.

The second sidewall 208 includes the second recess 212. The second recess 212 extends through the second sidewall 208. In an exemplary embodiment, the second recess 212 has a gradually decreasing width along a longitudinal length (L) (FIG. 2C) of the second sidewall 208 such that a first width ($W_1$) is greater than a second width ($W_2$).

The second sidewall 208 may further include a fastener 232 similar to the fastener 228 configured to be attachable to a tool for moving the receiver member 200. In an exemplary embodiment, the fastener 232 is a groove. The second sidewall 208 further includes an aperture 234 similar to the aperture 228 which is in communication with the second recess 212. In an exemplary embodiment, the aperture 234 is formed on an outside wall 236 of the receiver member 200.

Figure 2A:
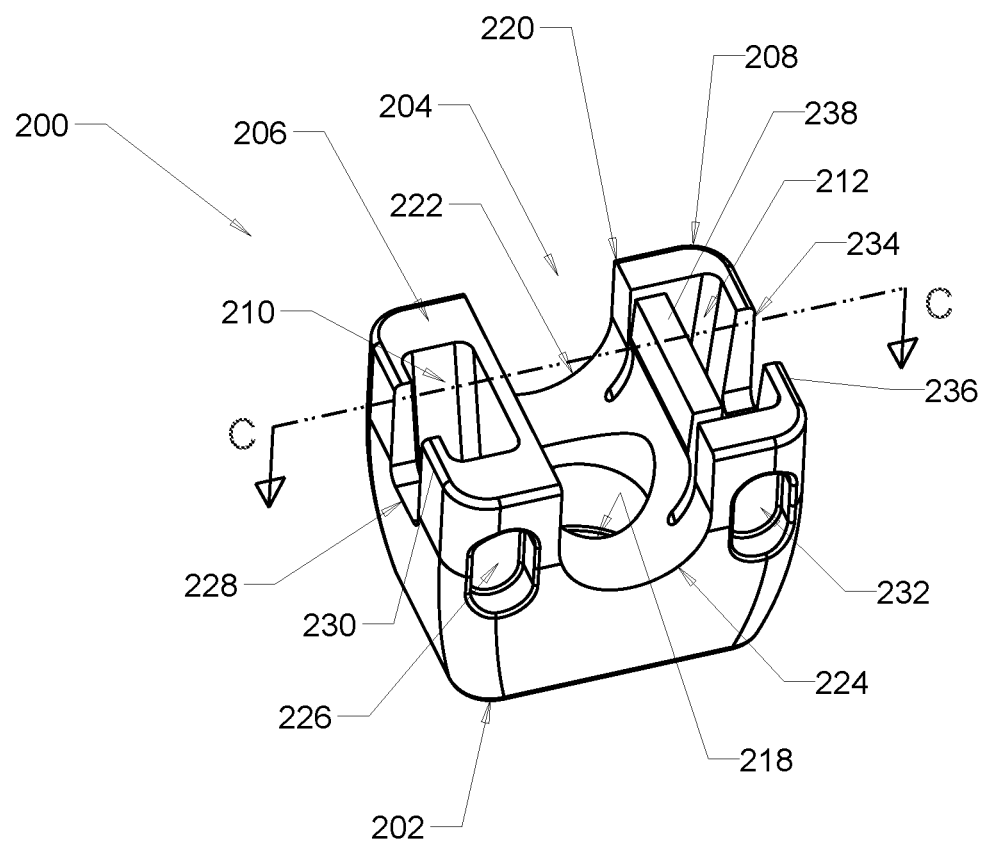
FIG. 2A is a perspective view of a receiver member of the exemplary embodiment of FIG. 1A.
Figure 2B:
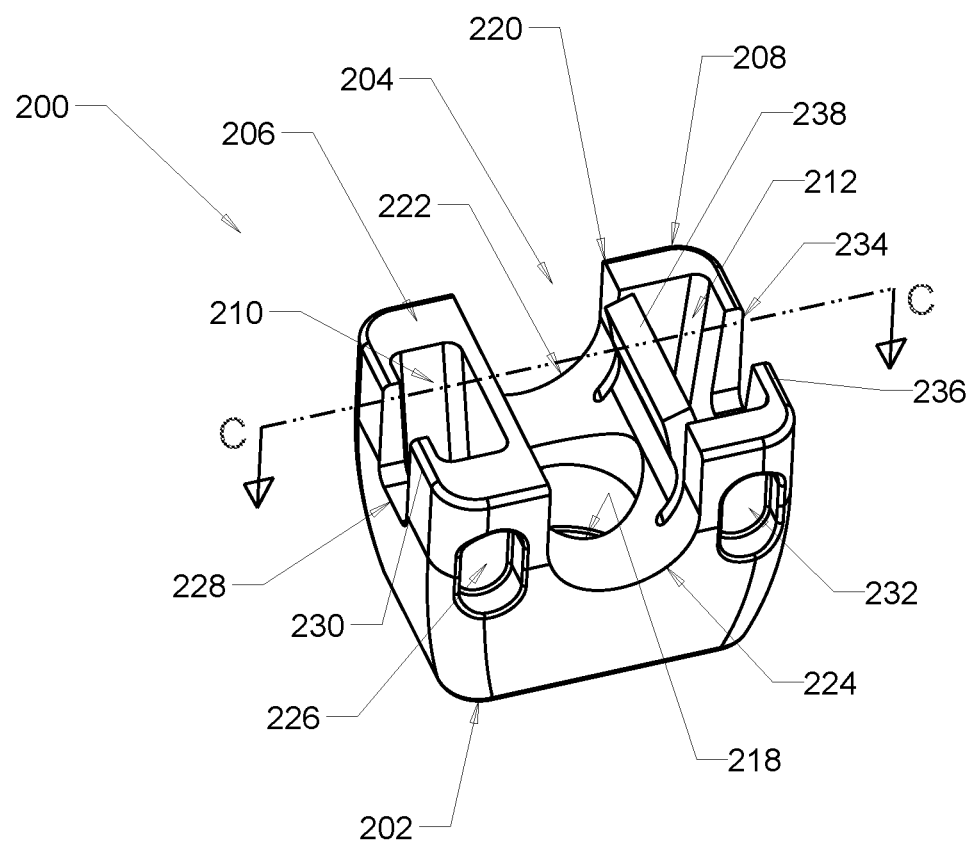
FIG. 2B is a perspective view of the receiver member of FIG. 2A.
Figure 2C:
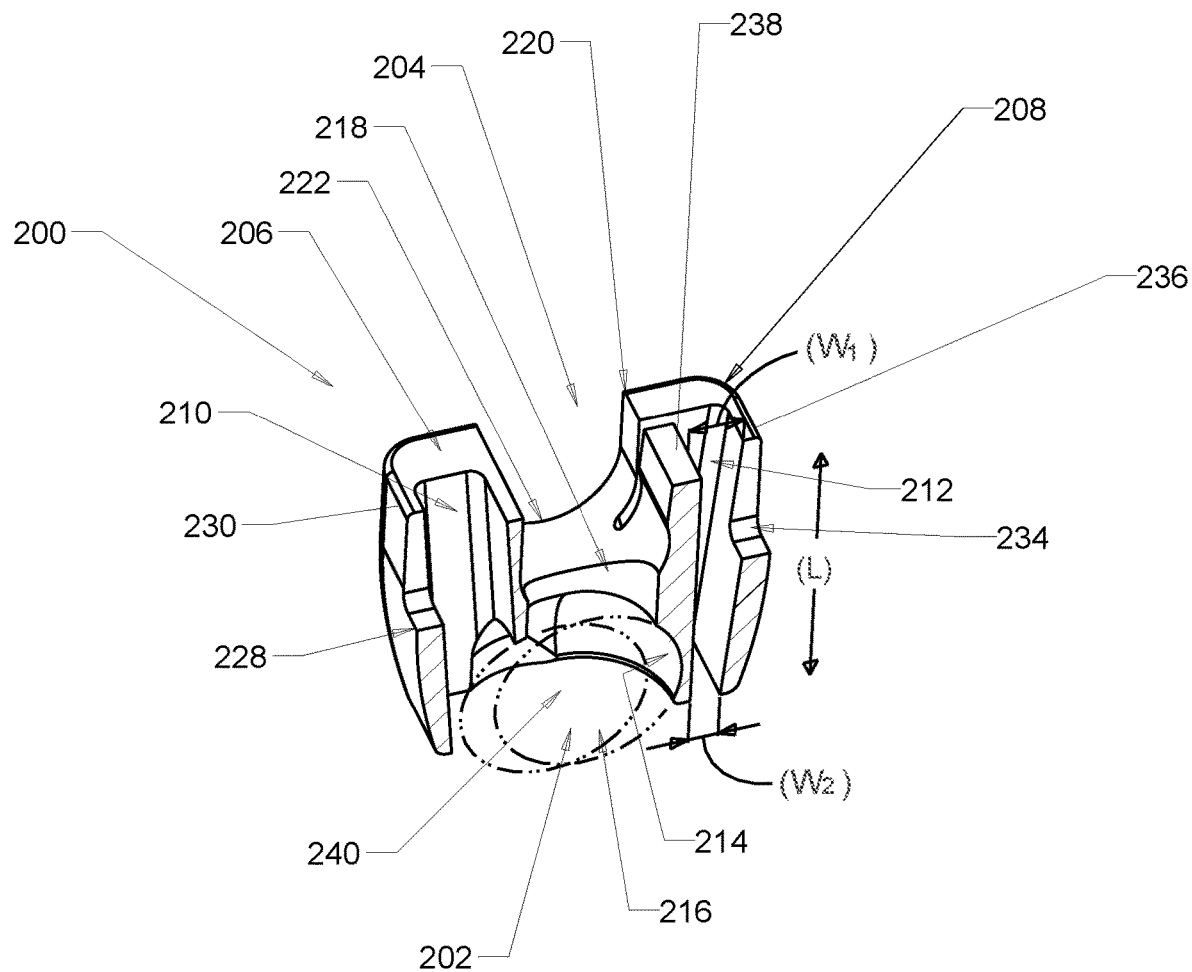
FIG. 2C is a cross-sectional perspective view of the receiver member of FIG. 2A taken along C-C.
Figure 3A:
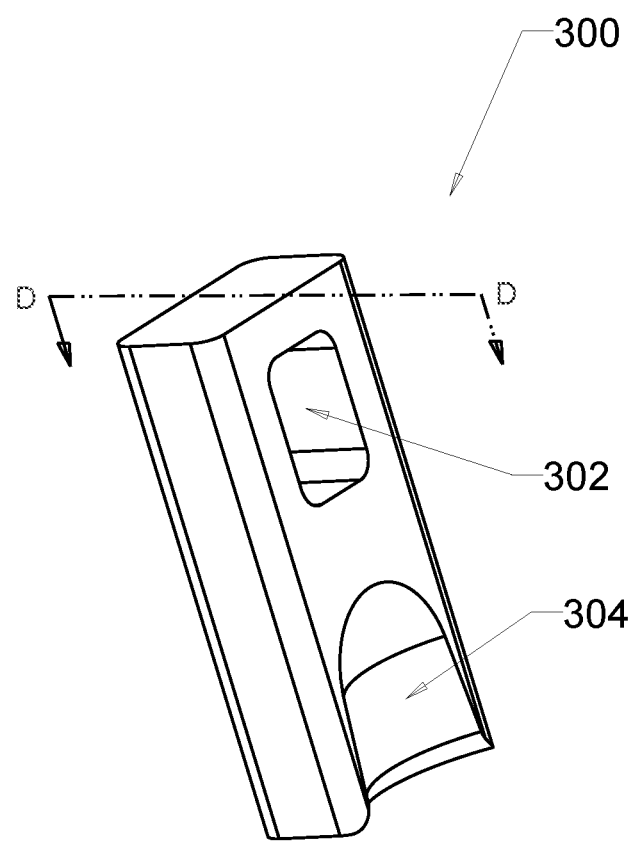
FIG. 3A is a perspective view of a shank locking member in accordance with an exemplary aspect of the exemplary embodiment of FIG. 1A.
Figure 3B:
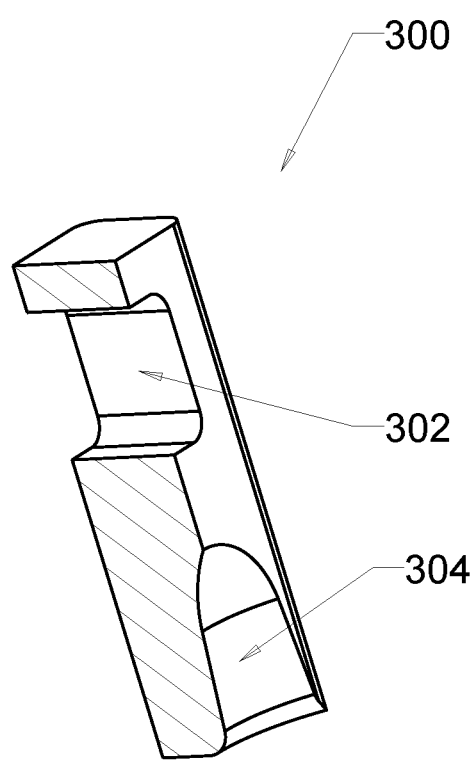
FIG. 3B is a cross-sectional perspective view of FIG. 3A taken along D-D.
Figure 4A:
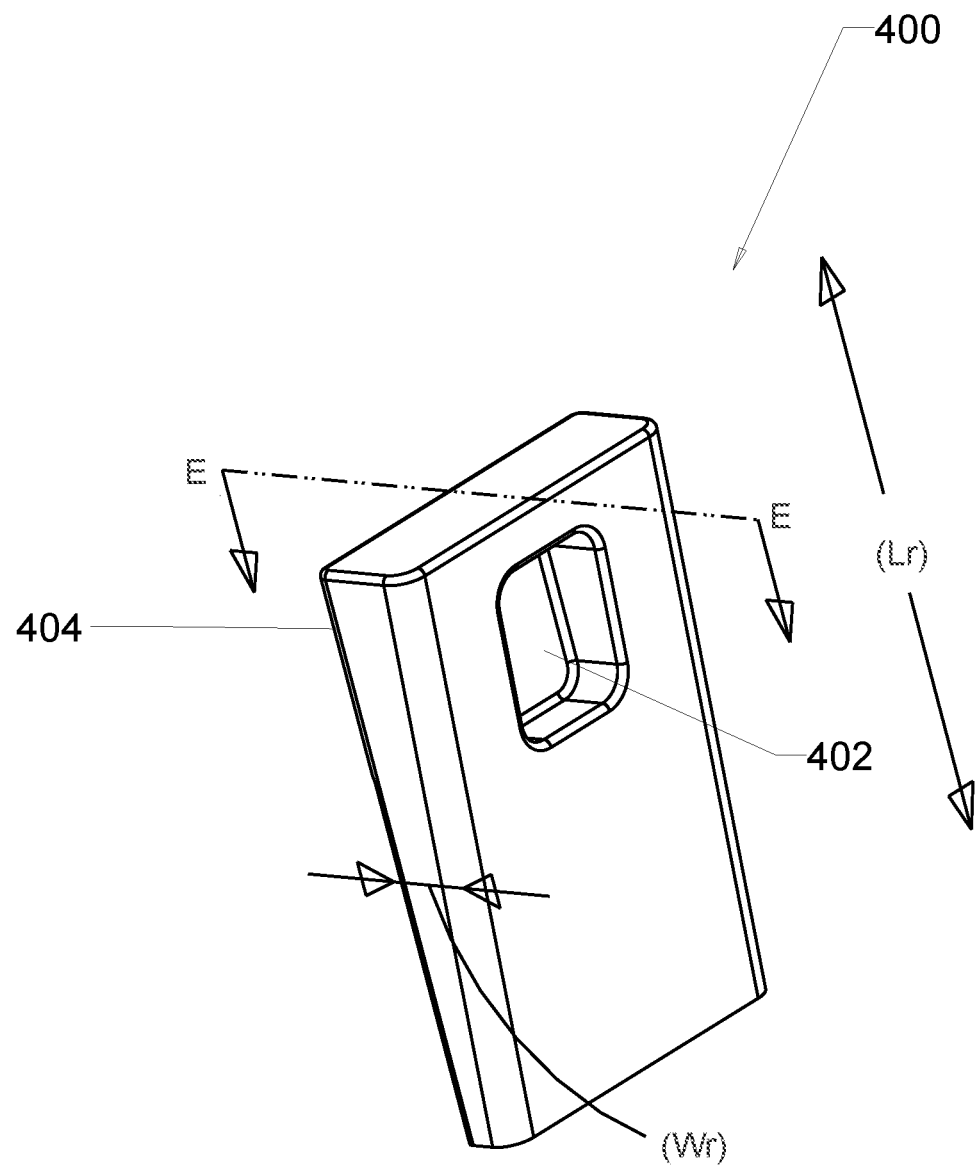
FIG. 4A is a perspective view of a rod locking member in accordance with an exemplary aspect of the exemplary embodiment of FIG. 1A.
Figure 4B:
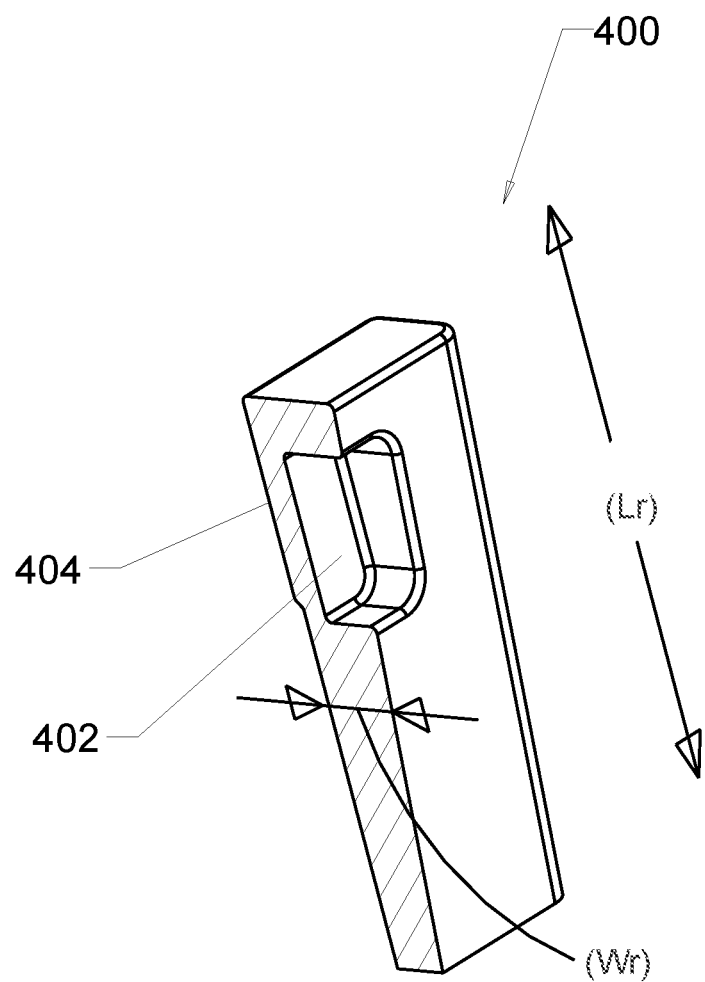
FIG. 4B is a cross-sectional perspective view of FIG. 4A taken along E-E.

The second sidewall 208 further includes a movable portion 238 adjacent to the rod receiving recess 204. As shown in FIGS. 2A and 2B, the movable portion 238 is movable between a first position (FIG. 2A) and a second position (FIG. 2B). When moved into the second position, the movable portion 238 is configured to move into the rod receiving recess 204. In other words, the second sidewall is movable between first and second positions.

Figure 5A:
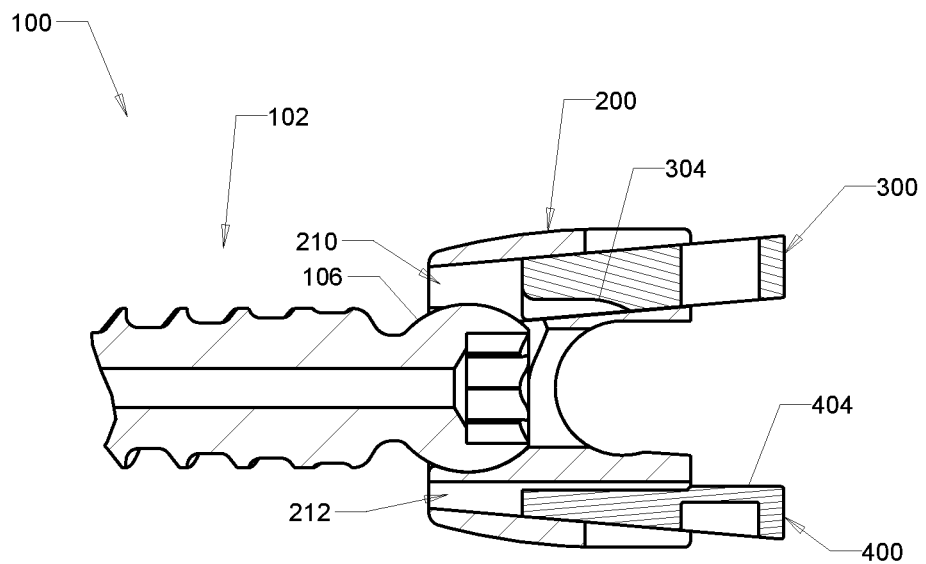
FIG. 5A is a cross-sectional view of a polyaxial bone anchor in accordance with an exemplary embodiment of the subject disclosure with a rod omitted and in an unlocked state.
Figure 5B:
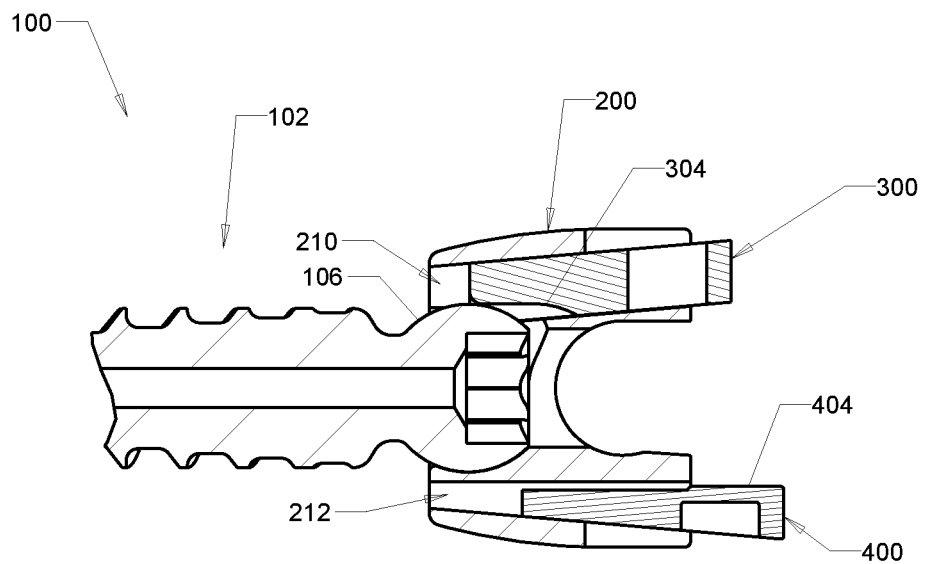
FIG. 5B is a cross-sectional view of the polyaxial bone anchor of FIG. 5A showing a first locking member in an partially engaged state.
Figure 5C:
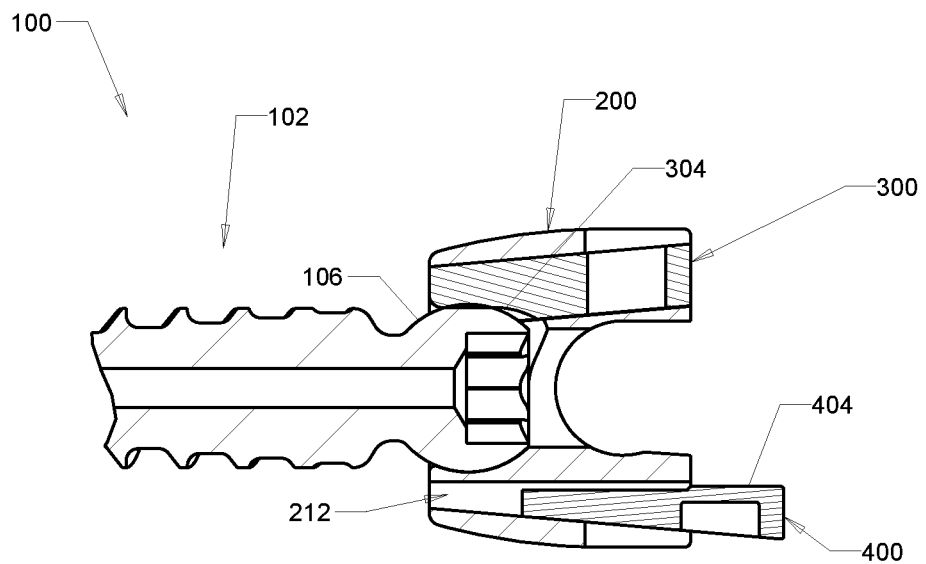
FIG. 5C is a cross-sectional view of the polyaxial bone anchor of FIG. 5B showing the first locking member in a fully engaged locking position.

Referring now to FIGS. 1A-1D, 3A and 3B, the first locking member 300 is configured substantially as shown. The first locking member 300 is sized and shaped to be slidably movable within the first recess 210 of the receiver member 200. The first locking member 300 includes an aperture 302 and a concave portion 304. The aperture 302 is configured to overlap with the aperture 228 of the first sidewall 206 when the first locking member 300 is inserted into the first recess 210 for facilitating removal from or insertion into the first recess 210 via, e.g., a surgical instrument. The concave portion 304 is sized and shaped to engage the rounded head 106 of the shank 102. Specifically, as shown in FIGS. 5B-5C, when the shank 102 is positioned inside the open bottom end 202, the concave portion 304 is sized and shaped to move passed the rounded head 106 and frictionally engage the rounded head 106 when fully inserted into the second recess 212. In other words, the first locking member 300 functions as a shank locking member wedge for securing the rounded head 106.

In sum, the polyaxial bone anchor comprises a receiver member that includes an open bottom for receiving a shank having a substantially spherical head, a first locking member, and a first sidewall having a first recess configured to receive the first locking member. The first locking member includes a curved surface configured to engage the substantially spherical head of the shank when the shank is received within the open bottom. The first locking member is a locking wedge.

Referring now to FIGS. 1A-1D, 4A and 4B, the second locking member 400 is configured substantially as shown. The second locking member 400 is sized and shaped to be slidably moveable within the second recess 212 of the receiver member 200. In an exemplary embodiment, the second locking member 400 is a sloped locking member having a slope along a longitudinal length (Lr) such that a width (Wr) is greater at one end of the second locking member compared to an opposite end of the second locking member. The portion of the second locking member 400 that has a greater width (Wr) than the first width ($W_1$) of the second sidewall 208 is configured to move the movable portion 238 of the second sidewall 208 when inserted into the second recess 212.

The second locking member 400 includes a groove 402 and a protruding portion 404. The groove 402 is configured to overlap with the aperture 234 of the second sidewall 208 when the second locking member 400 is inserted into the rod receiving recess 212 for facilitating removal from or insertion into the second recess 212 via, e.g., a surgical instrument. The protruding portion 404 is located near the end having the greater width (Wr) along the longitudinal length (Lr) and is configured to press against the movable portion 238 of the second sidewall 208. In other words, the receiver member further includes a second sidewall having a second recess configured to receive a second locking member.

Referring now to FIGS. 1A-1D, the shank 102 is configured substantially as shown. The shank 102 includes the head 106 and a body 108. The body 108 extends downward or distally from the head 106. Although the body 108 is illustrated in the exemplary embodiment as integrally formed with the head 106 as a unitary piece, the head and body can alternatively be separate components coupled together. The shank 102 also includes a protrusion 110 such as a thread. The protrusion 110 extends from a lateral side of the body 108 and along a longitudinal length (Ls) of the body 108.

In an exemplary embodiment, the head 106 of the shank 102 is substantially spherical. Alternatively, the head 106 of the shank 102 is generally elongated or oblong in cross-section and insertable into the open bottom end 202 of the receiver member 200 in one orientation and not insertable in another orientation. The head 106 is preferably curved convexly and includes grooves 112. As best shown in FIG. 1D, the head 106 has a star-shaped recess that is sized to be generally complementary to a head of a driver, e.g., a screwdriver. Other recess shapes, such as rectangular, hexagonal, slotted, and convex may be used, as well as other structures known to be useful in receiving a driving tool.

Figure 12:
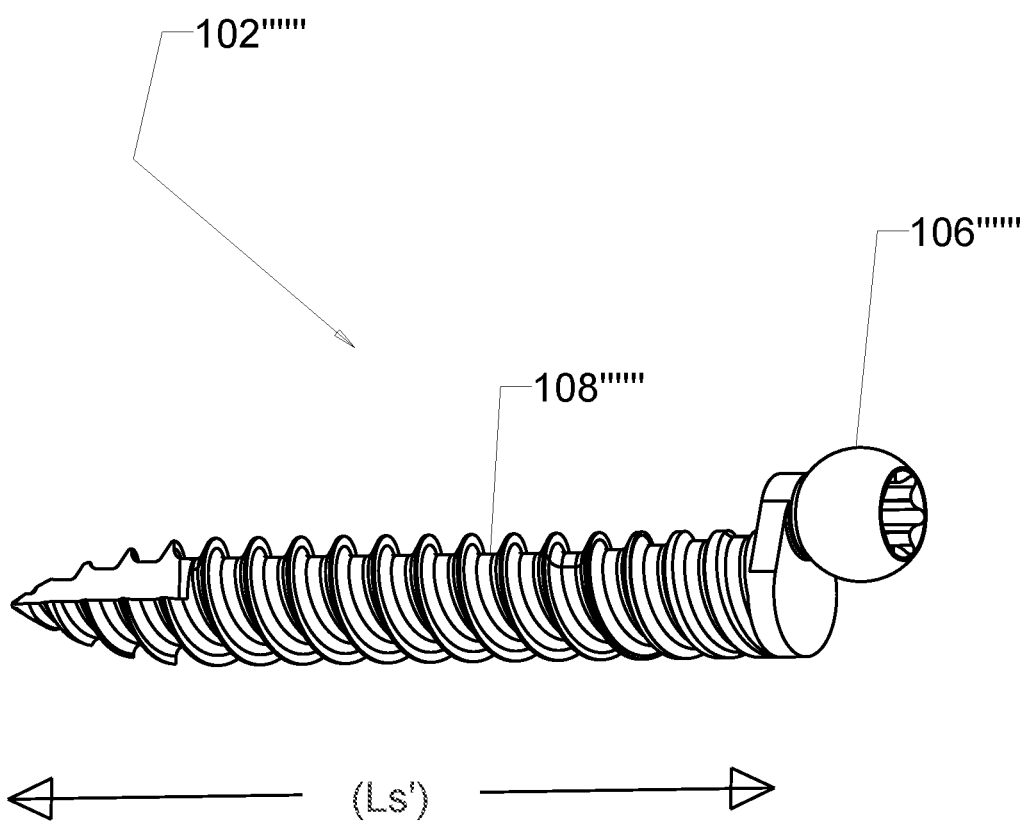
FIG. 12 is a perspective view of an exemplary embodiment of an eccentric screw applicable to the exemplary embodiments of the subject disclosure.

It is appreciated that the shank can take other shapes and forms to accommodate positioning along a patient's lumbar spine. For example, as shown in FIG. 12, an eccentric shank 102'''' is disclosed and configured substantially as shown. Specifically, the eccentric shank 102'''' has a head 106'''' offset from a longitudinal length (Ls') of the shank body 108''''. In other words, the shank includes a shank body and the rounded head is offset from a longitudinal axis of the shank body.

Figure 1B:
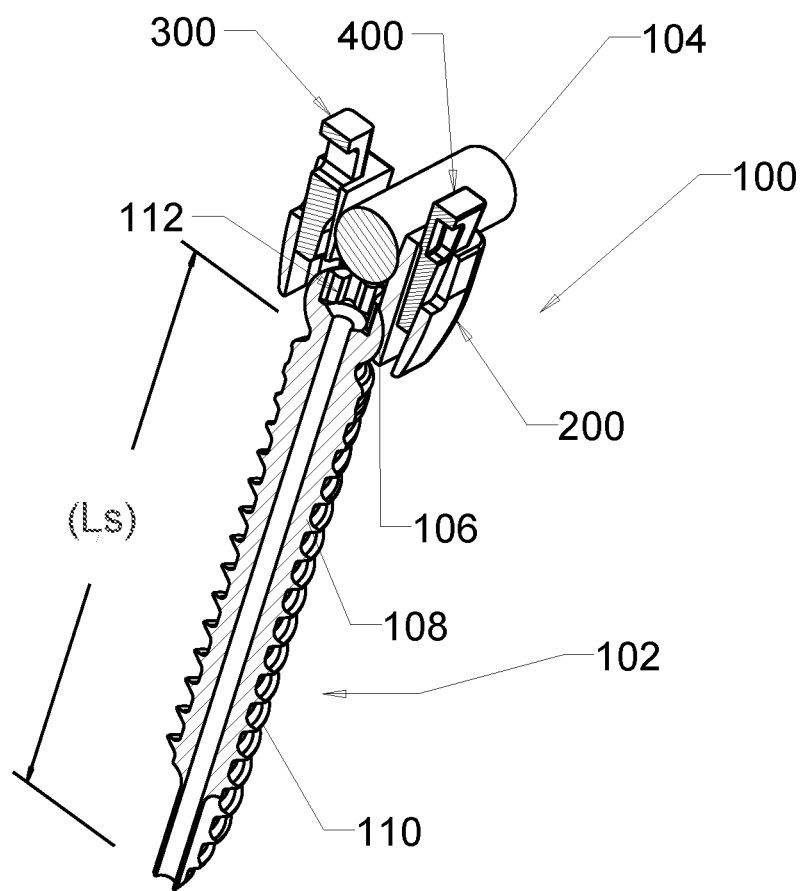
FIG. 1B is a cross-sectional view of FIG. 1A taken along A-A.
Figure 1C:
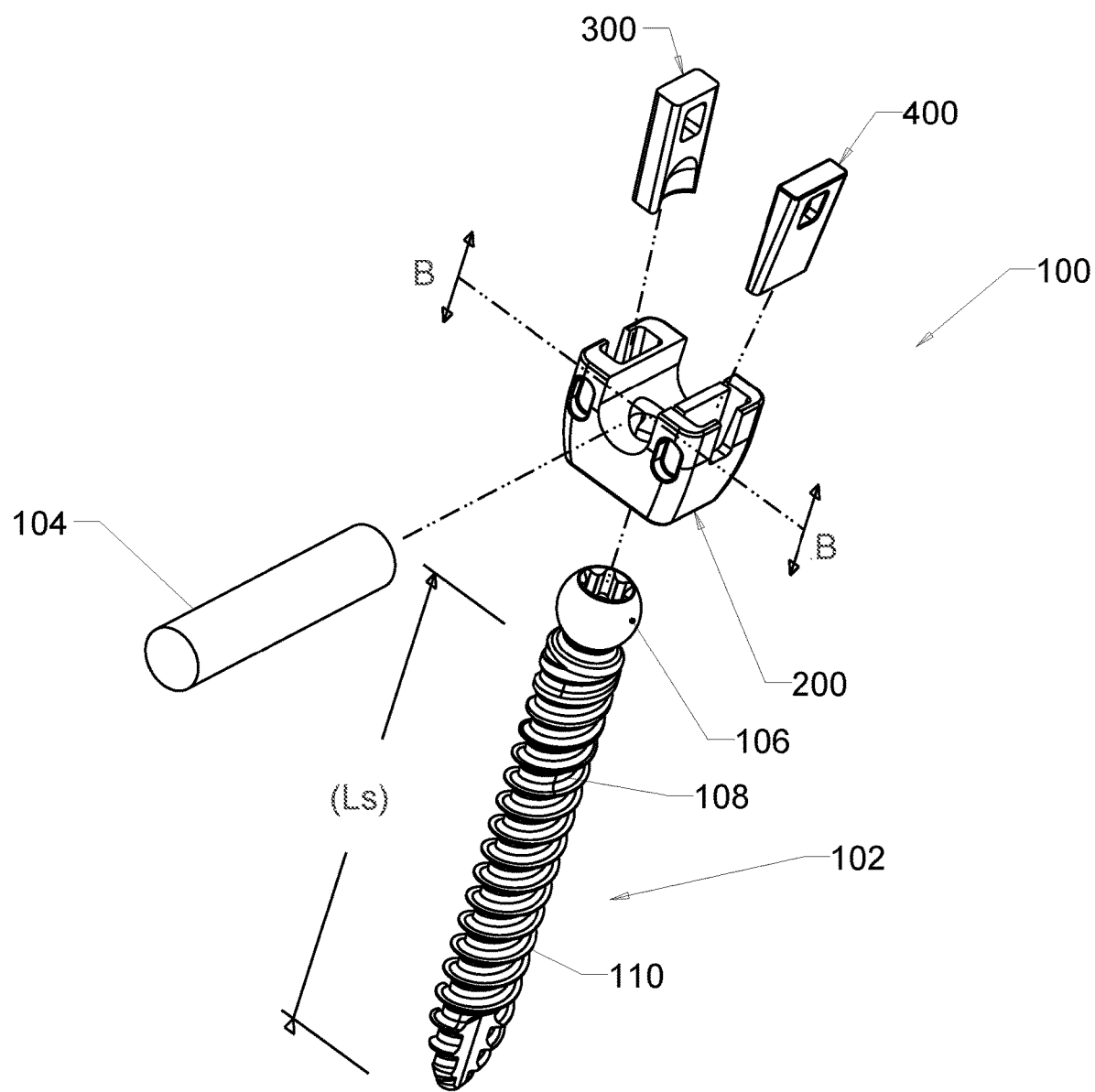
FIG. 1C is an exploded view of FIG. 1A.
Figure 1D:
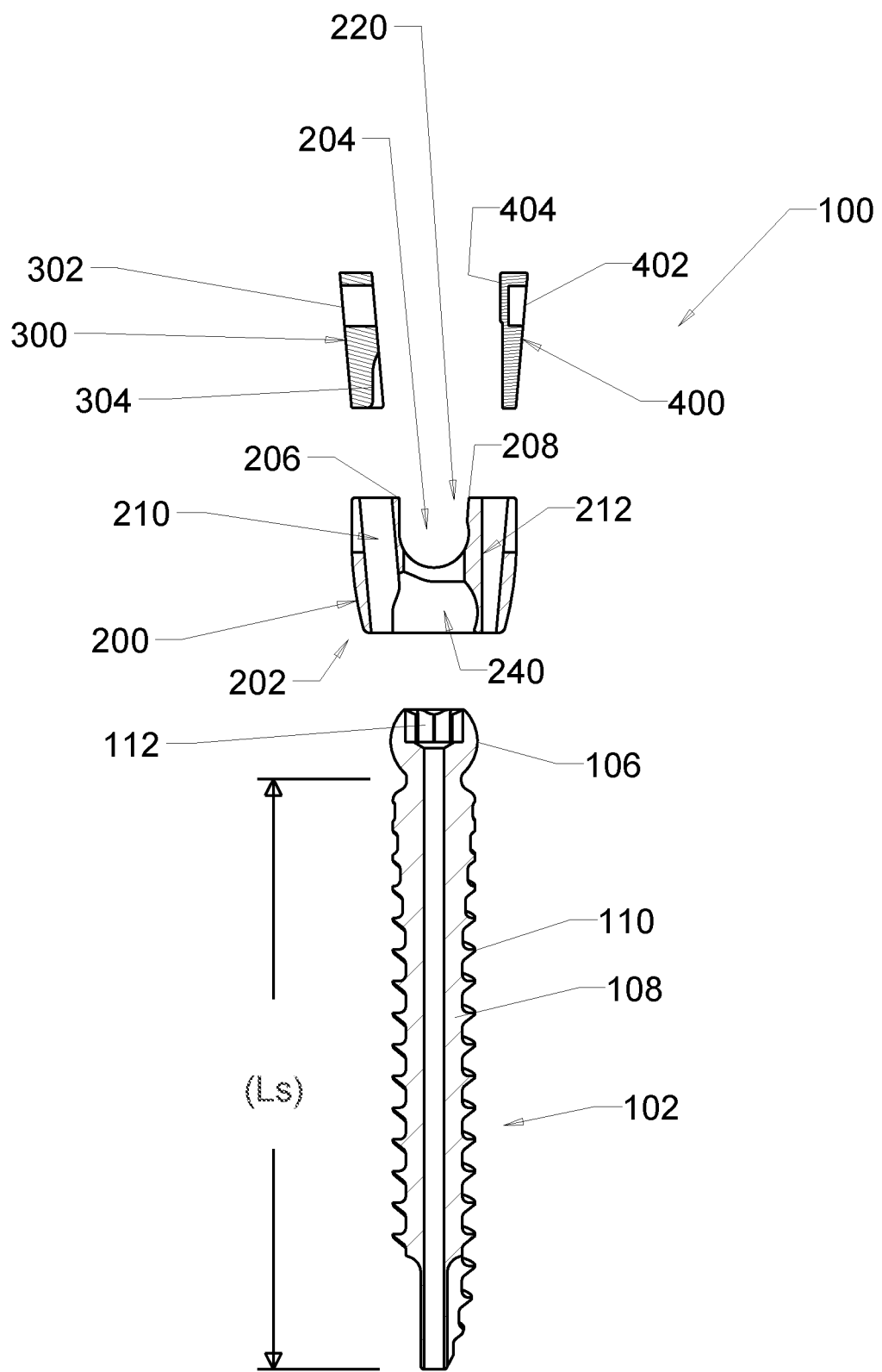
FIG. 1D is an exploded cross-sectional view of FIG. 1C taken along B-B with a rod omitted.

Referring now to FIGS. 1A-1C, the rod 104 is configured substantially as shown. The rod 104 is an elongated and generally cylindrical member. It is appreciated that other cross-sectional shapes are contemplated including oval, rectangle, and irregular shapes. The rod 104 is illustrated as straight, however it may have a lordotic curve or be otherwise bent or curved. The rod 104 may have any desired length sufficient for its intended purpose.

Figure 6A:
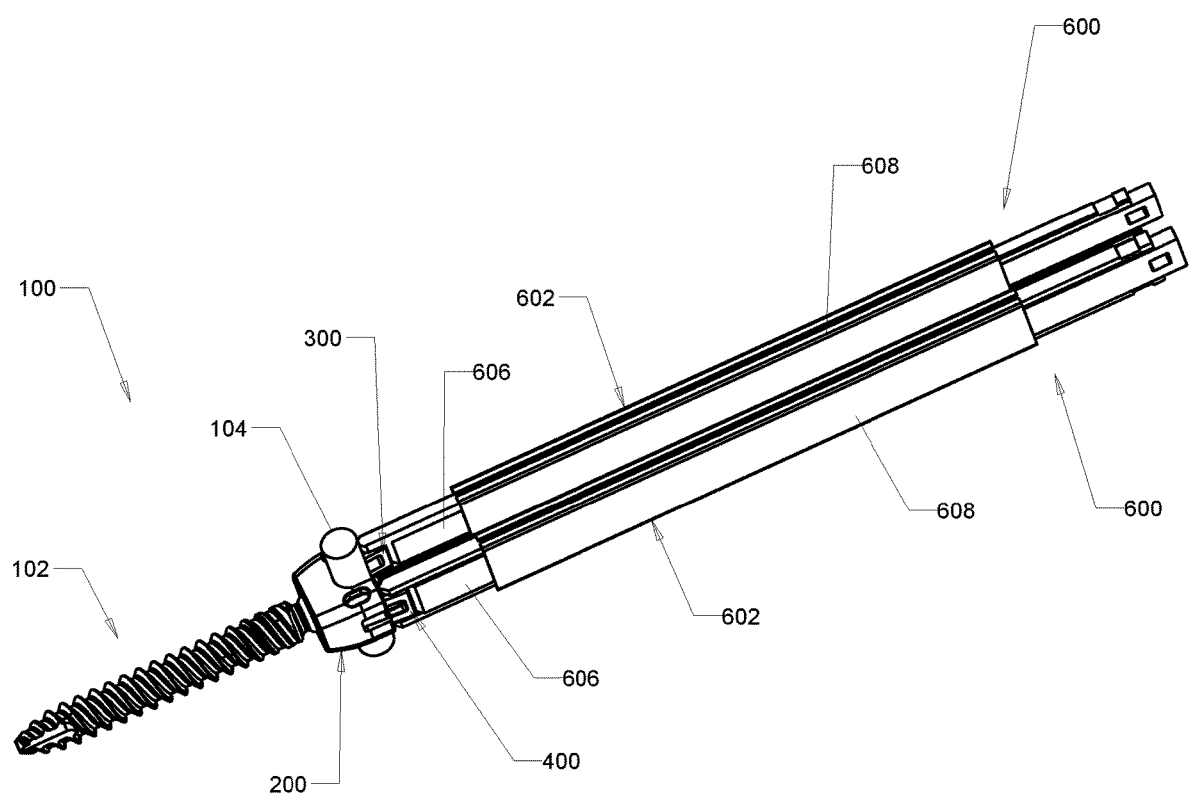
FIG. 6A is a perspective view of a polyaxial bone anchor in accordance with an exemplary embodiment of the subject disclosure.
Figure 6B:
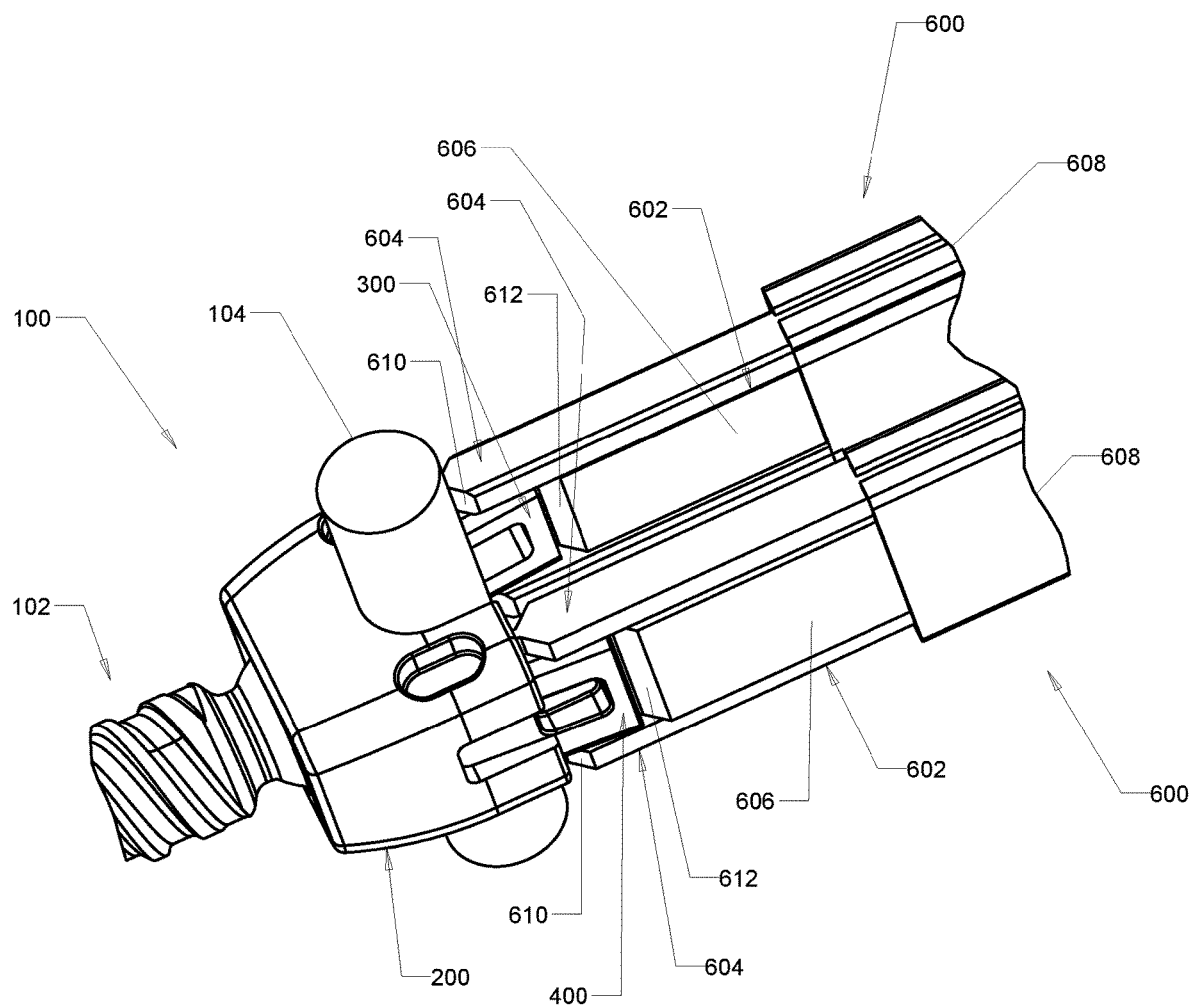
FIG. 6B is an enlarged perspective view of the polyaxial bone anchor of FIG. 6A.

Referring now to FIGS. 6A and 6B, the percutaneous driver 600 is configured substantially as shown. The percutaneous driver 600 includes an elongated body 602 with a proximal end 604 and a driver 606. The proximal end 604 is configured to attach to the receiver member 200. The driver 606 is configured to slide along the elongated body 602. In an exemplary embodiment, the driver 606 is configured to push against one of the first locking member 300 or second locking member 400. Additionally, in an exemplary embodiment, the driver 606 is rigidly attachable to one of the first locking member 300 and second locking member 400.

The percutaneous driver 600 can further include a guide 608 or other mechanism to facilitate the sliding motion of the driver 606 in a direction along which the locking members 300, 400 enter the respective recesses 210, 212. The percutaneous drivers 600 are further configured to be detachable from the receiver member 200 and the locking members 300, 400 by way of, e.g., weakened portions 610, 612 along the elongated body 602 and the driver 606 where the elongated body and driver connect to the receiver member and locking members, respectively. As such, the percutaneous driver 600 is configured to be able to "break away" by way of force after the polyaxial bone anchor 100 is secured to the patient.

In other words, the polyaxial bone anchor further comprises a percutaneous driver including an elongated body having a proximal end connected to the receiver member, and a driver connected to the first locking member and slidable along the elongated body. The percutaneous driver is connected to the receiver member about a weakened portion for separating from the receiver member. The percutaneous driver is connected to the first locking member about a weakened portion for separating from the first locking member.

Referring back to FIGS. 1A-6B, the polyaxial bone anchor 100 is configured as shown. The head 106 of the shank 102 is configured to be inserted into the open bottom end 202 of the receiver member 200. The shank 102 has polyaxial motion while within the open bottom end 202. The first locking member 300 is configured to be slidable within the first recess 210 for engaging the head 106 of the shank 102 with the concave portion 304 when inserted into the recess 210.

The rod 104 is configured to be inserted into the rod receiving recess 204 via the open top portion 220 of the rod receiving recess 204 and to be slidable through and along the diametrically opposed slots 222, 224. The second locking member 400 is configured to be slidable within the second recess 212 for engaging the movable portion 238 of the second sidewall 208 with the protruding portion 404 of the second locking member 400.

The percutaneous driver 600 is configured to rigidly attach to the receiver member 200 at about the proximal end 604 of the percutaneous driver. The driver 606 of the percutaneous driver 600 is configured to slide along the elongated body 602 and serve as a means to apply a force against first and second the locking members 300, 400, respectively, for moving the locking members into their respective recesses 210, 212.

As best shown in FIGS. 5A-5F, an exemplary embodiment of the polyaxial bone anchor 100 operates by providing two independent locking mechanisms for the shank 102 and the rod 104.

The shank head 106 is first inserted into the open bottom end 202 of the receiver member 200. However, it is appreciated that the shank can either be already secured to the patient or free-floating relative to the patient. It is further appreciated that the shank head 106 can be accessed via the open top portion 218 for operating purposes thereof.

When the shank 102 is positioned in the desired orientation, the first locking member 300 is inserted into the first recess 210. As the first locking member 300 is inserted deeper into the recess 210, the concave portion 304 begins to contact the shank head 106 and limit the motion of the first locking member 300. As shown in FIG. 5B, when the first locking member 300 reaches the section of the open bottom end 202 wherein the open bottom end and the first recess 210 overlap, the shank head 106 cannot be removed from the open bottom end 202 but still retains polyaxial motion. As shown in FIG. 5C, when the first locking member 300 is further inserted into the recess 210, the concave portion 304 fully contacts the shank head 106 and creates an interference fit for the shank head 106 between the receiver member 200 and the first locking member 300. Thus, the shank 102 is locked in position. If the operator of the polyaxial bone anchor 100 decides to reorient the shank 102, the operator can pull on the aperture 302 of the first locking member 300 to disengage it from the shank.

In other words, the first locking member is slidable within the first recess. The first locking member is configured to directly engage the substantially spherical head of the shank when the first locking member is received within the first recess and the shank is received within the open bottom. The first locking member is configured to press-fittingly engage the substantially spherical head when the shank is received within the open bottom.

Figure 5D:
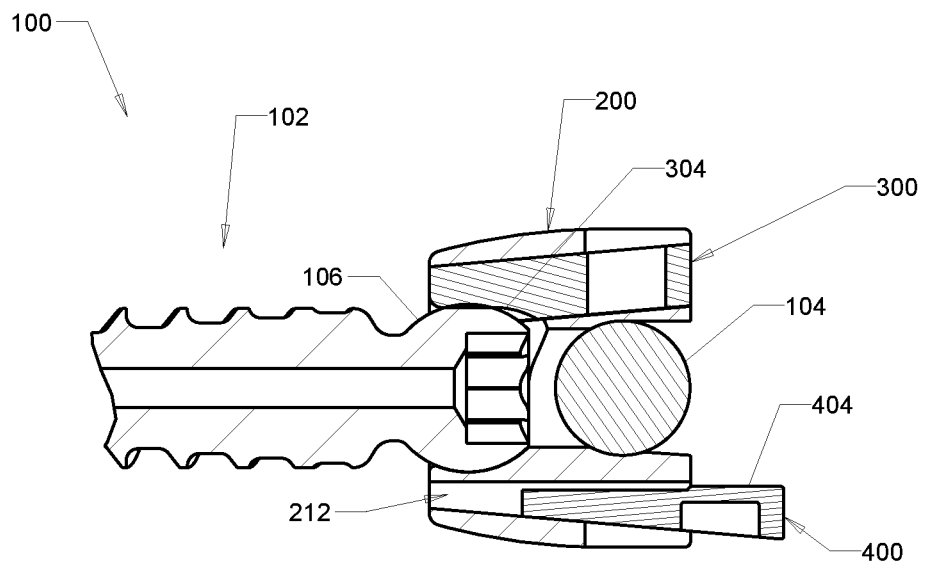
FIG. 5D is a cross-sectional view of the polyaxial bone anchor of FIG. 5C showing a rod and a second locking member in an unlocked state.
Figure 5E:
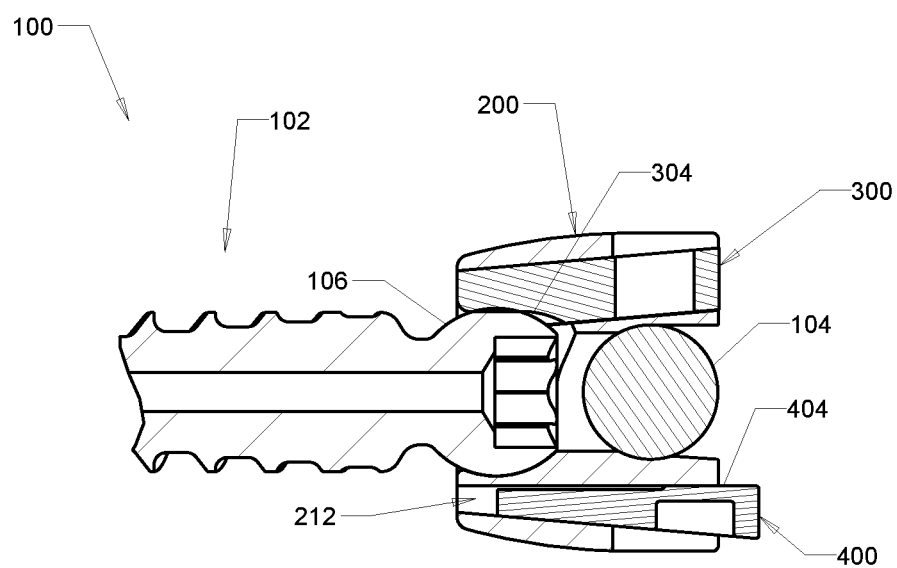
FIG. 5E is a cross-sectional view of the polyaxial bone anchor of FIG. 5D showing the second locking member in a partially engaged state.
Figure 5F:
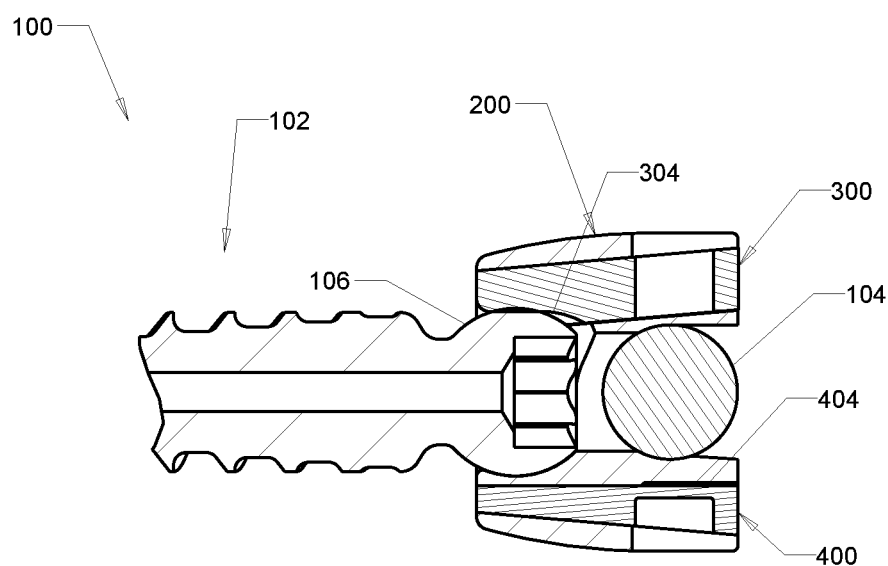
FIG. 5F is a cross-sectional view of the polyaxial bone anchor of FIG. 5E showing the second locking member in a fully engaged locking position.

As shown in FIGS. 5D-5F, when the shank 102 is secured, the rod 104 can be inserted into the receiver member 200 through the diametrically opposing walls 222, 224 or the open top portion 220. When the rod 104 is in its desired position, for example in connection with another polyaxial bone anchor, the second locking member 400 is inserted into the second recess 212. As the second locking member 400 is inserted deeper into the second recess 212, the movable portion 238 of the second sidewall 208 is pushed out. As the movable portion 238 is pushed out, the movable portion 238 presses against the rod 104 and creates an interference fit for the rod 104 to be secured therewith. If the operator of the polyaxial bone anchor 100 decides to reorient the rod 104, the operator can pull on the groove 402 of the second locking member 400 to disengage it from the rod.

In other words, the receiver member includes a first press-fit locking mechanism for engaging the shank and a second press-fit locking mechanism for engaging the rod. The receiver member further includes a body having a first recess and a second recess, wherein the first press-fit locking mechanism comprises the first recess and a first locking member, and the second press-fit locking mechanism comprises the second recess and a second locking member. The body further includes a rod receiving recess for receiving the rod. The rod receiving recess is positioned between the first and second press-fit locking mechanisms. Also, the second locking member is configured to press-fittingly engage the second recess. The rod receiving recess is positioned between the first and second press-fit locking mechanisms.

The advantages of having independent locking mechanisms for a rod and a shank of a polyaxial pedicle anchor are apparent. Specifically, the above disclosure teaches a friction based locking mechanism which achieves desired goals of, e.g., high polyaxial locking strength, high oscillation angle, high fatigue strength, and so forth. Further, both the shank and the rod can be independently adjusted to effect compression, distraction and derotation of the spine if necessary without undo hassle. The design also allows for use of eccentric screws which allow for a greater range of applications along the spine.

Additionally, the polyaxial bone anchor is well equipped to be used in conjunction with robots which increases efficiency. Specifically, the disclosed locking mechanisms do not rely on tactile sensations to confirm whether the polyaxial bone anchor is secured. Efficiency can be further increased with multiple robot arms working on multiple polyaxial bone anchors using pre-programmed motions.

It is appreciated that the subject disclosure can be altered without deviating from the scope of the subject disclosure. For example, FIGS. 7-11B disclose additional exemplary embodiments.

Figure 7:
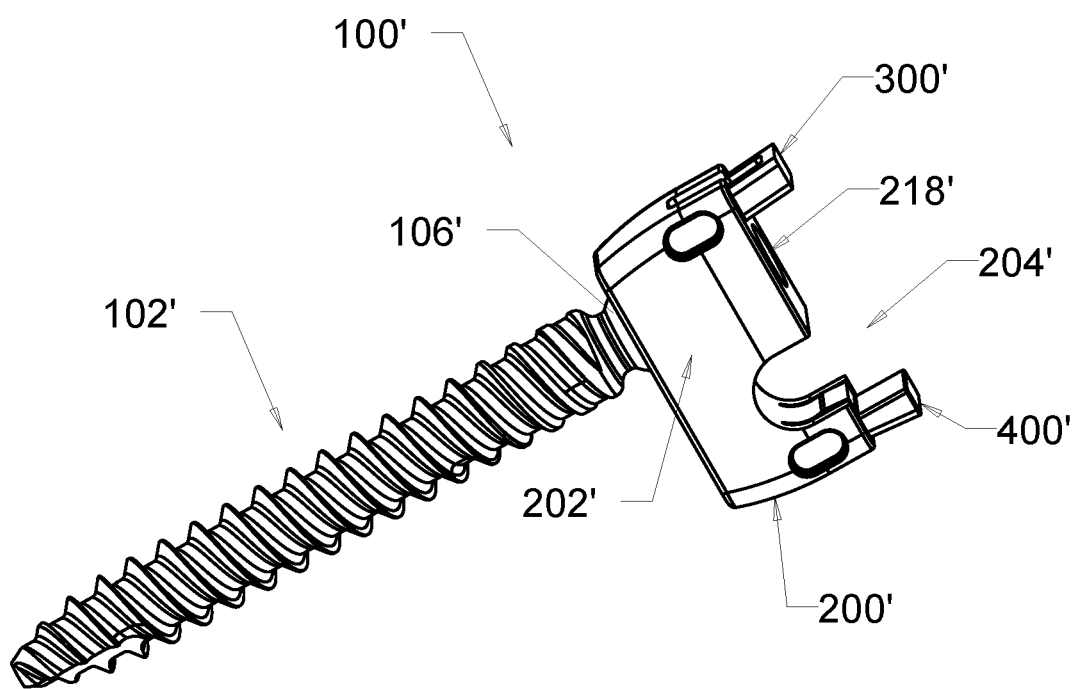
FIG. 7 is a perspective view of a polyaxial bone anchor in accordance with an exemplary embodiment of the subject disclosure with a rod omitted.

Referring now to FIG. 7, a polyaxial bone anchor 100' is configured substantially as shown. The polyaxial bone anchor 100' includes an open bottom end 202' and a rod receiving recess 204' offset from the open bottom end. It is appreciated that the open bottom end 202' includes an open top portion 218' that extends through a receiver member 200' so that a head 106' of a shank 102' can be accessed through the receiver member 200'.

It is appreciated that having a shank locking mechanism independent from a rod locking mechanism makes this concept ideal for an offset type of screw, where the rod does not have to be directly over the shank. This is useful in cases where the patient's anatomy does not allow for perfect alignment of the screw to the rod construct.

Figure 8:
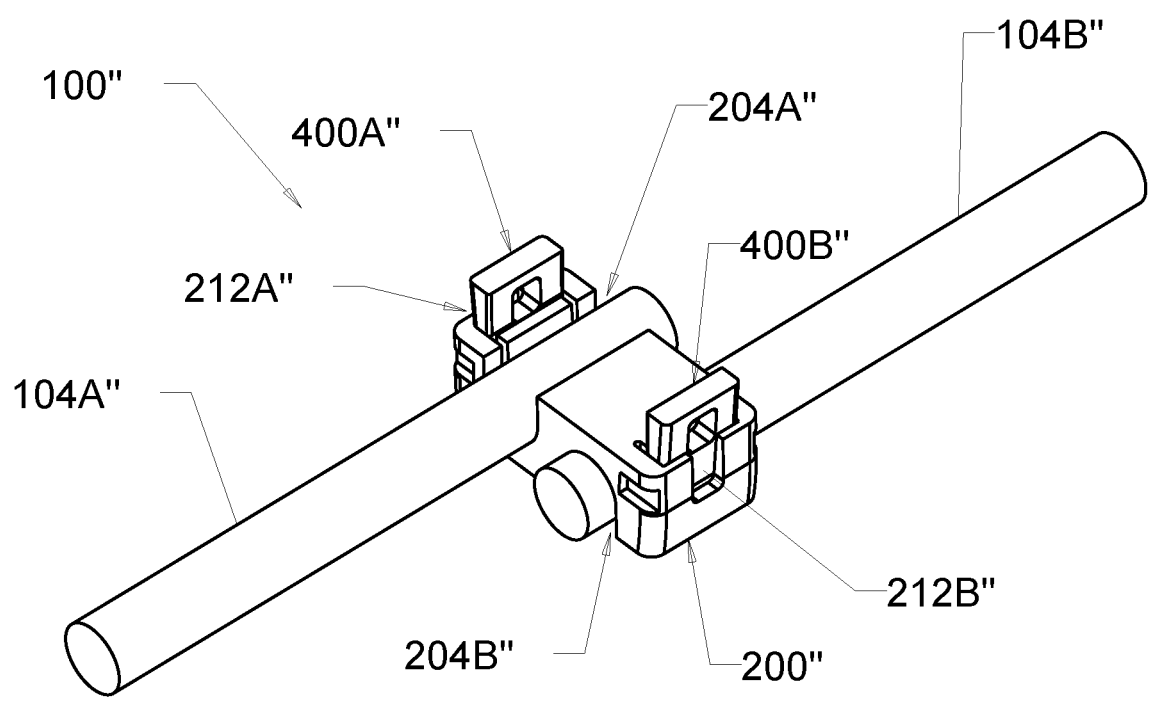
FIG. 8 is a perspective view of a rod connector in accordance with an exemplary embodiment of the subject disclosure.

Referring now to FIG. 8, a rod-to-rod connector 100" is configured substantially as shown. The rod-to-rod connector 100" functions to connect two separate rods 104A", 104B" of separate polyaxial bone anchors. The rod-to-rod connector 100" includes a receiver member 200" having a first recess 212A" and a second recess 212B" with corresponding first and second locking members 400A", 400B". The receiver member 200" further includes rod receiving recesses 204A", 204B" that are adjacent to one another. In an exemplary embodiment, one of the rod receiving recesses 204A" faces downwardly and the other of the rod receiving recesses 204B" faces upwardly.

In other words, the rod connector comprises a first receiver member portion that includes a first rod receiving recess for receiving a first rod, a first locking member and a first sidewall having a first recess for receiving the first locking member. The first sidewall is movable between first and second positions. The rod connector further comprises a second receiver member portion adjacent the first receiver member portion, the second receiver member portion includes a second rod receiving recess for receiving a second rod, a second locking member, and a second sidewall having a second recess for receiving the second locking member. The first rod receiving recess is formed by the first sidewall, and the second rod receiving recess is formed by the second sidewall. Each of the first sidewall and the second sidewall is movable between first and second positions.

A key advantage to the rod-to-rod connector 100" is that the rod-to-rod connector can be placed directly down onto a rod as shown in FIG. 8. Therefore, no top-loading locking cap is required. Additionally, the rod-to-rod connector can be used in conjunction with one or more polyaxial bone anchors by acting as a bridge between separate polyaxial bone anchors. For example, because of the opposite-facing directions of the rod receiving recesses, the rod-to-rod connector would first be placed over a first screw-and-rod polyaxial bone anchor that was already implanted by placing the connector directly onto the rod with no need to "hook" under the rod or go over the end of the rod. The second rod would then be placed down into the up-facing rod receiving recess, which can thereby be connected to another screw-and-rod polyaxial bone anchor.

Figure 9:
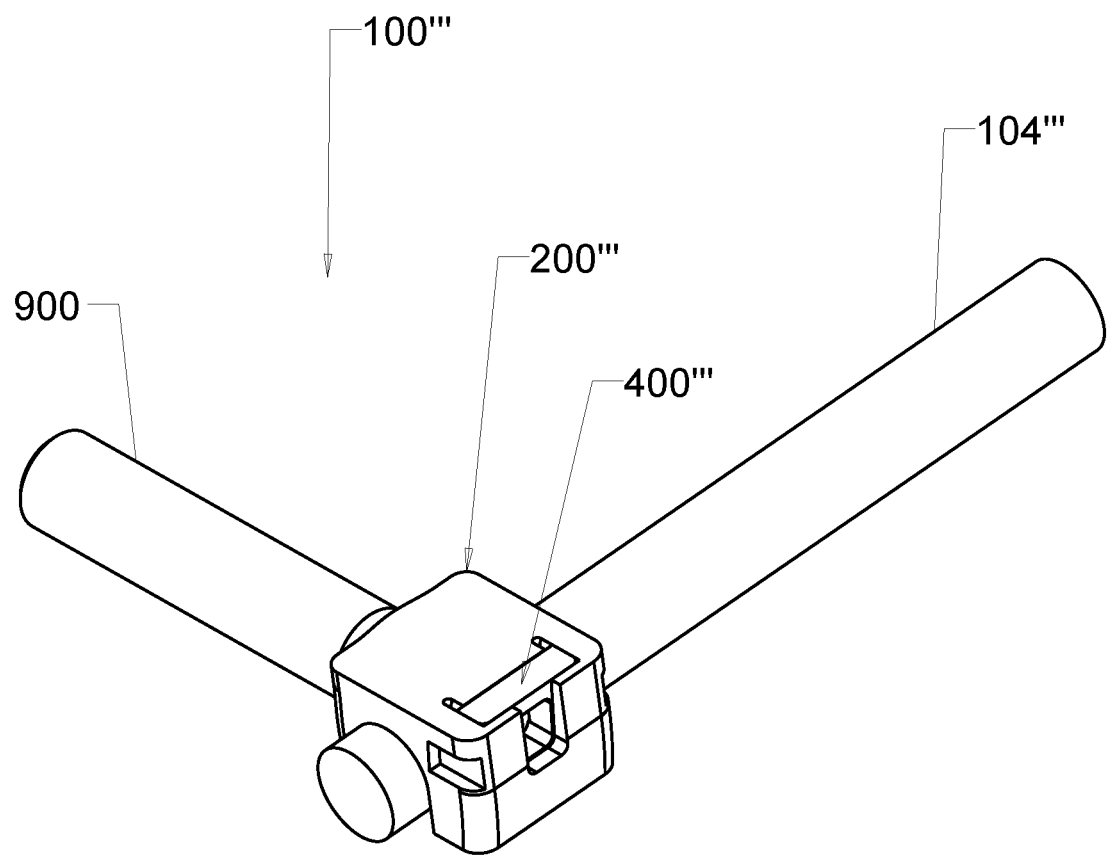
FIG. 9 is a perspective view of another rod connector in accordance with exemplary embodiment of the subject disclosure.

Referring now to FIG. 9, a rod-to-rod connector 100''' is configured substantially as shown. The rod-to-rod connector 100''' functions as a lateral offset rod connector by having a rod 900 integrally formed with a receiver member 200'''. As such, a rod 104''' can be attached to the receiver member 200''' as described above using a second locking member 400''' and thereby forming a laterally offset rod connector.

Such lateral offset connectors are commonly used to connect polyaxial bone anchors with, e.g., an iliac screw. In such a use, the lateral offset connector would be dropped onto the iliac screw and the polyaxial bone anchor, which would both already be implanted.

Figure 10:
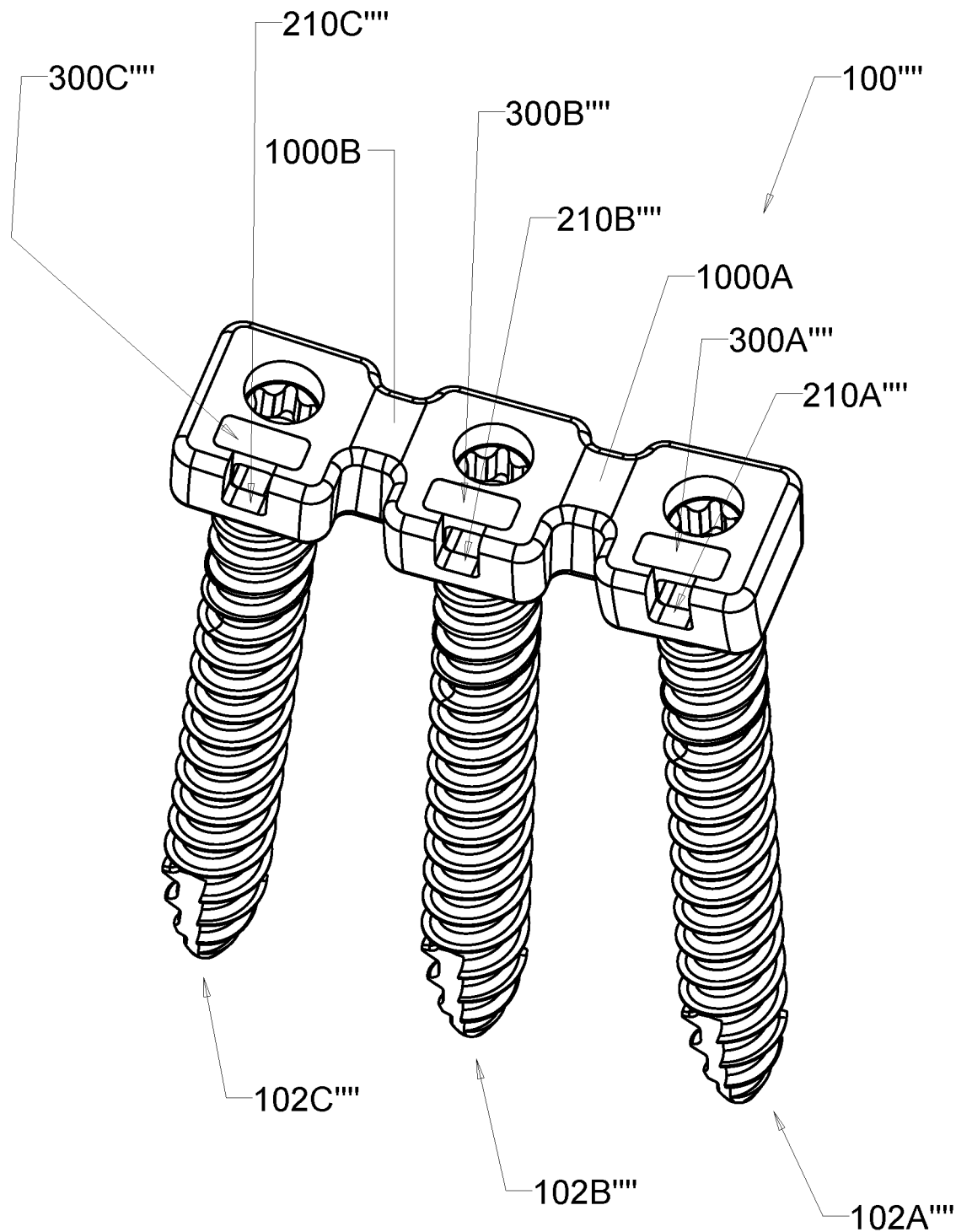
FIG. 10 is a perspective view of another bone anchor system in accordance with an exemplary embodiment of the subject disclosure.

Referring now to FIG. 10, a polyaxial bone anchor system 100'''' is configured substantially as shown. The polyaxial bone anchor system 100'''' functions as a rodless pedicle screw system. The polyaxial bone anchor system 100'''' includes a plurality of interconnected shanks 102A'''', 102B'''', 102C'''', first locking members 300A'''', 300B'''', 300C'''' and first recesses 210A'''', 210B'''', 210C''''. The shanks, locking members and recesses are interconnected via connecting members 1000A, 1000B extending between receiver members 200A'''', 200B'''', 200C''''. In an exemplary embodiment, the connecting members 1000A, 1000B are integrally formed with the receiver members 200A'''', 200B'''', 200C''''. It is appreciated that any number of receiver members can be interconnected in such a way.

Figure 11A:
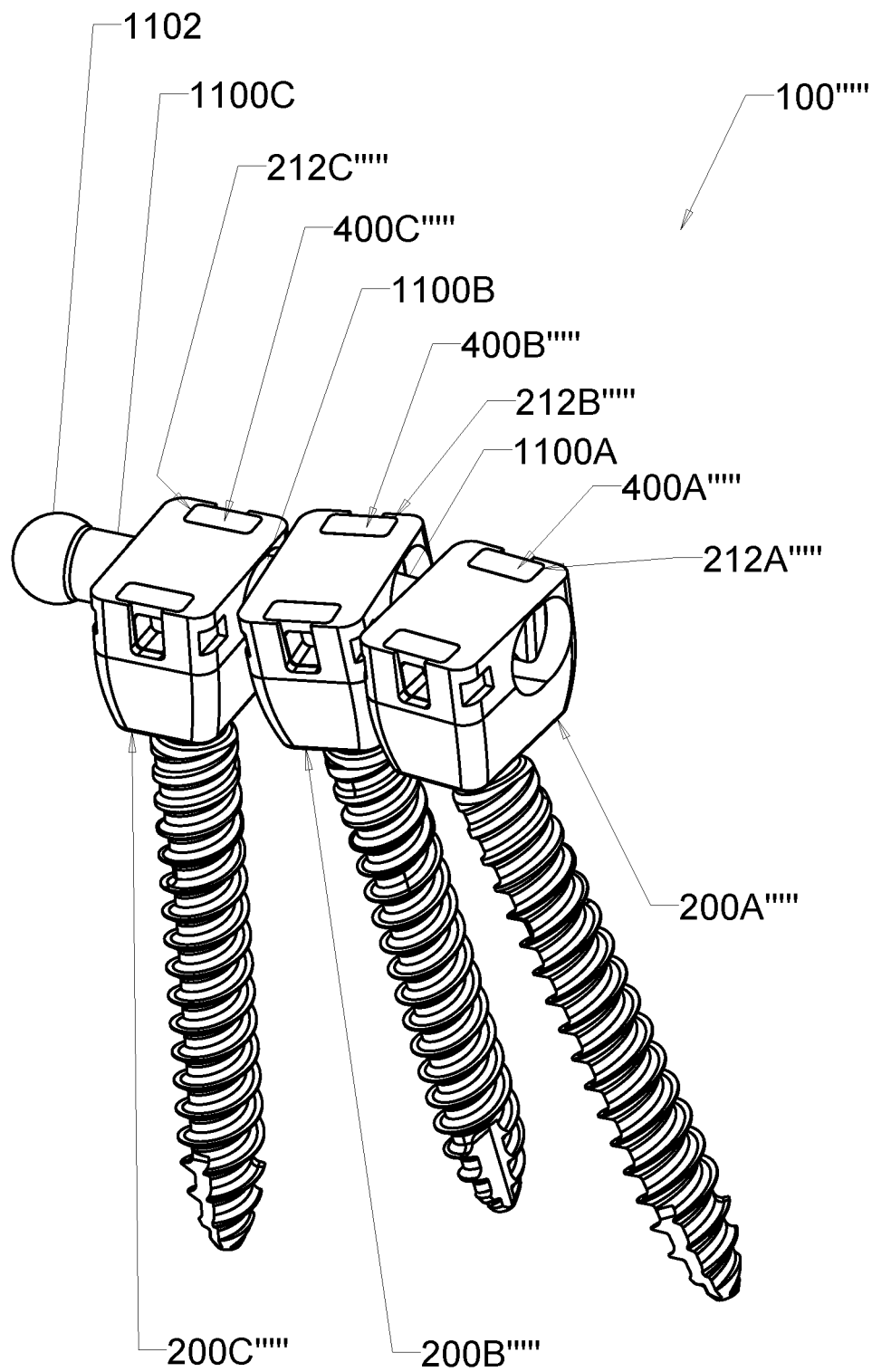
FIG. 11A is a perspective view of another bone anchor system in accordance with an exemplary embodiment of the subject disclosure.
Figure 11B:
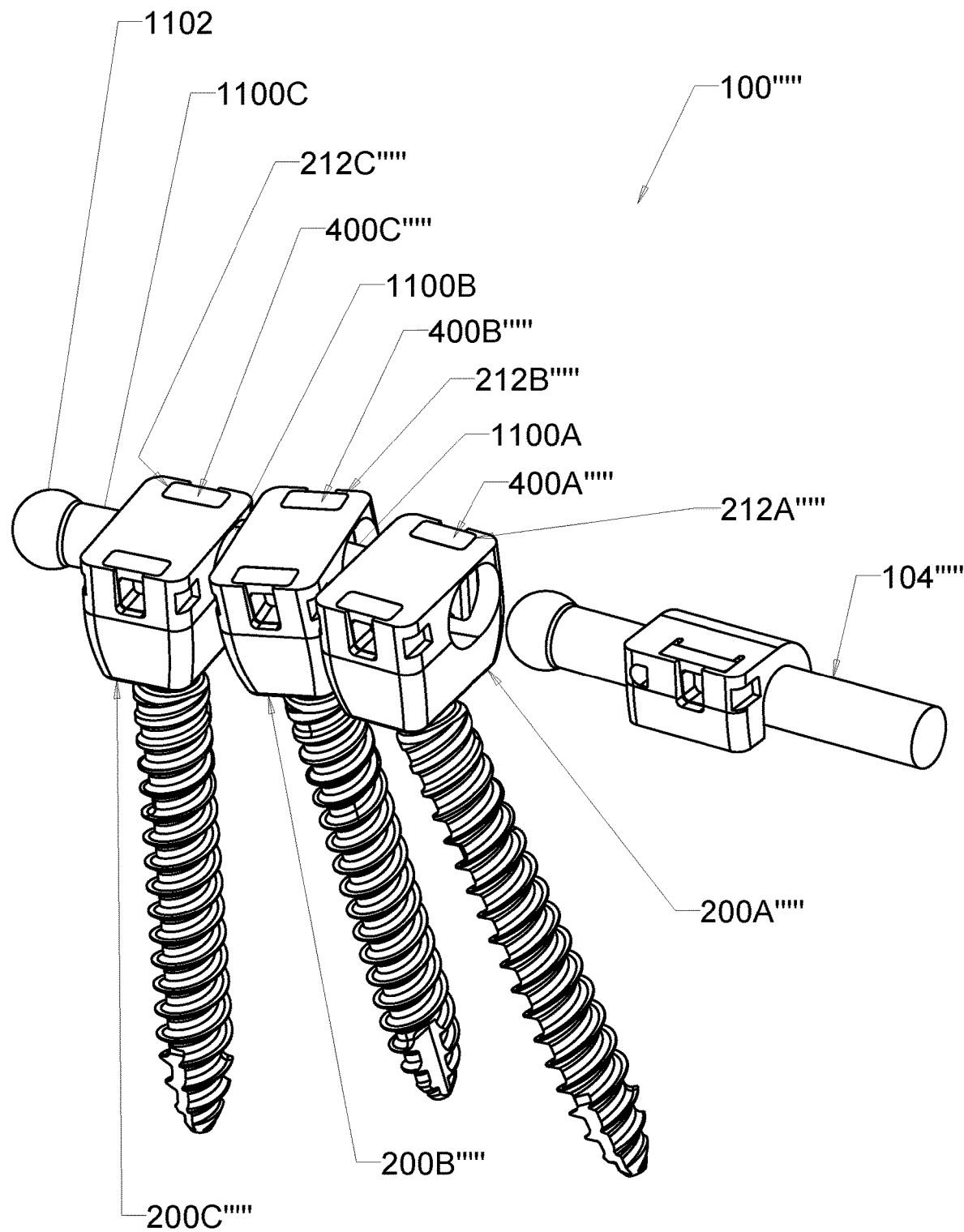
FIG. 11B is a perspective view of the bone anchor system of FIG. 11A with a rod.

Referring now to FIGS. 11A and 11B, a polyaxial bone anchor system 100''''' is configured substantially as shown. The polyaxial bone anchor system 100''''' functions a sectional jointed pedicle bone anchor fixation system. The polyaxial bone anchor system 100''''' includes connecting members 1100A, 1100B, 1100C having rounded ends 1102 for connecting to the second recesses 212A''''', 212B''''', 212C''''' of a plurality of receiver members 200A''''', 200B''''', 200C'''''. The second recesses 212A''''', 212B''''', 212C''''' are configured to receive the rounded end 1102 at each of the diametrically opposed slots (not shown) that define the second recesses 212A''''', 212B''''', 212C''''', as discussed above. Thus, until the rounded ends 1102 are secured by second locking members 400A''''', 400B''''', 400C''''', the receiver members 200A''''', 200B''''', 200C''''' have some polyaxial motion that can accommodate for shank misalignment between the receiver members. Further, a rod 104''''' can be attached at one of the end the receiver members 200A''''', 200B''''', 200C''''' and attached thereto to other receiver members if necessary.

While the subject disclosure has been described with reference to exemplary embodiments, it will be appreciated by those skilled in the art that various changes may be made and equivalents may be substituted for elements thereof without departing from the scope of the exemplary embodiments. For example, features described in one embodiment may be incorporated into a different embodiment, such as the type of shank or rod used. Additionally, features described in one manner may instead be accomplished by known techniques in the art, such as the type of shank used.

In addition, modifications may be made to adapt a particular situation or material to the teachings of the various embodiments without departing from the essential scope thereof. For example, the rods can be configured to only be "top loaded" as opposed to be passing through the lateral sides of the receiver member. It is to be understood, therefore, that the exemplary embodiments not be limited to the particular aspects disclosed, but it is intended to cover modifications within the spirit and scope of the exemplary embodiments as defined by the appended claims.

The invention claimed is:

1. A polyaxial bone anchor comprising:
   a receiver member that includes:
      an open bottom for receiving a shank having a substantially spherical head,
      a first locking wedge,
      a first sidewall having a first through hole configured to press-fittingly receive the first locking wedge, and
      a second sidewall.

2. The polyaxial bone anchor of claim 1, wherein the second sidewall includes a second through hole configured to receive a second locking wedge.

3. The polyaxial bone anchor of claim 2, wherein the first locking wedge is a tapered locking wedge.

4. The polyaxial bone anchor of claim 2, wherein the second locking wedge extends into the second through hole and is configured to press-fittingly engage a substantially spherical head of a shank received within the open bottom.

5. The polyaxial bone anchor of claim 2, wherein the second locking wedge includes a curved surface configured to engage a substantially spherical head of a shank received within the open bottom.

6. The polyaxial bone anchor of claim 2, wherein the second through hole is in fluid communication with the open bottom.

7. The polyaxial bone anchor of claim 2, wherein the second sidewall includes a living hinge.

8. The polyaxial bone anchor of claim 2, wherein the second sidewall includes a pivotable wall portion.

9. The polyaxial bone anchor of claim 2, wherein the second through hole includes a distal opening spaced from the open bottom end.

10. The polyaxial bone anchor of claim 2, wherein the second through hole is larger than the first through hole.

11. The polyaxial bone anchor of claim 1, wherein the first sidewall is moveable between first and second positions.

12. The polyaxial bone anchor of claim 1, further comprising a percutaneous driver extending from the receiver member, the percutaneous driver including:
   an elongated body having a proximal end connected to the receiver member adjacent the first through hole; and
   a driver slidable relative to the elongated body for engaging the first locking wedge.

13. The polyaxial bone anchor of claim 12, wherein the percutaneous driver is connected to the receiver member about a weakened portion for separating from the receiver member.

14. The polyaxial bone anchor of claim 12, wherein the percutaneous driver is connected to the first locking wedge about a weakened portion for separating from the first locking wedge.

15. The polyaxial bone anchor of claim 12, wherein the driver is connected to the first locking wedge via a living hinge.

16. The polyaxial bone anchor of claim 1, wherein the first side wall is a unitarily formed wall.

17. The polyaxial bone anchor of claim 1, wherein the first side wall includes a first aperture in fluid communication with the first through hole.

18. The polyaxial bone anchor of claim 17, wherein the first side wall includes a second aperture in fluid communication with the first through hole.

19. A polyaxial bone anchor system comprising:
   a shank having a rounded head;
   a rod; and
   a receiver member that includes:
      a first press-fit wedge directly engageable with the shank, and
      a second press-fit wedge for press-fittingly engaging the rod,
   wherein the first press-fit wedge engages the shank independently from the second press-fit wedge engaging the rod.

20. The polyaxial bone anchor system of claim 19, wherein the receiver member further includes a body having a first through hole and second through hole, wherein the first press-fit wedge is received within the first through hole, and wherein the second press-fit wedge is received within the second through hole.

21. The polyaxial bone anchor system of claim 20, wherein the body further includes a rod receiving recess for receiving the rod.

22. The polyaxial bone anchor system of claim 21, wherein the rod receiving recess is positioned between the first and second press-fit wedges.

23. The polyaxial bone anchor system of claim 20, wherein the shank further includes a shank body, and wherein the rounded head is offset from a longitudinal axis of the shank body.

24. A rod connector comprising:
   a first receiver member portion that includes:
      a first rod receiving recess for receiving a first rod,
      a first locking wedge, and
      a first sidewall having a first pocket for receiving the first locking wedge, wherein the first pocket includes a first pivotable wall for engaging the first rod; and
   a second receiver member portion adjacent the first receiver member portion, the second receiver member portion includes:
      a second rod receiving recess for receiving a second rod,
      a second locking wedge, and
      a second sidewall having a second pocket for receiving the second locking wedge, wherein the second pocket includes a second pivotable wall for engaging the second rod.

25. The rod connector of claim 24, wherein the first rod receiving recess is formed by the first sidewall, and wherein the second rod receiving recess is formed by the second sidewall.

26. The rod connector of claim 24, wherein the first pivotable wall is formed as a living hinge.

27. The rod connector of claim 24, wherein the first side wall includes a first aperture in fluid communication with the first pocket.

28. A polyaxial bone anchor comprising:
   a receiver member that includes:
   an open bottom for receiving a shank having a substantially spherical head, a first locking wedge having a through hole aperture and a curved surface configured to engage the substantially spherical head of the shank received within the open bottom,
   a first sidewall having a first through hole configured to receive the first locking wedge, and
   a second sidewall.

* * * * *